US012076185B2

(12) United States Patent
Stalter et al.

(10) Patent No.: US 12,076,185 B2
(45) Date of Patent: Sep. 3, 2024

(54) REVERSIBLE CART MOUNTED STORAGE BIN

(71) Applicant: GE Precision Healthcare LLC, Wauwatosa, WI (US)

(72) Inventors: Ross Christopher Stalter, Hartland, WI (US); Emily Elizabeth Siira, Waukesha, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 741 days.

(21) Appl. No.: 17/166,368

(22) Filed: Feb. 3, 2021

(65) Prior Publication Data
US 2022/0240894 A1    Aug. 4, 2022

(51) Int. Cl.
*A61B 8/00*    (2006.01)
*B62B 3/00*    (2006.01)

(52) U.S. Cl.
CPC .......... *A61B 8/4405* (2013.01); *A61B 8/4427* (2013.01); *B62B 3/008* (2013.01)

(58) Field of Classification Search
CPC ... A61B 8/4405; A61B 8/4411; A61B 8/4427; A61B 8/4433; A61G 12/001; B62B 3/008
See application file for complete search history.

(56) References Cited

U.S. PATENT DOCUMENTS

| | | | | |
|---|---|---|---|---|
| 3,963,126 A * | 6/1976 | Taub | ........................ | A47F 5/02 |
| | | | | 40/611.12 |
| 8,152,005 B2 * | 4/2012 | Barkdoll | ............... | A47F 5/0838 |
| | | | | 248/214 |
| 8,398,408 B1 * | 3/2013 | Hansen | ................ | A61B 8/4405 |
| | | | | 320/109 |
| 8,714,569 B2 * | 5/2014 | Lu | ............................. | B62B 3/02 |
| | | | | 280/35 |
| 9,180,898 B2 * | 11/2015 | Ninomiya | ............... | B62B 3/008 |
| 9,587,878 B2 * | 3/2017 | Paydar | .................... | G07F 9/002 |
| 9,933,106 B2 * | 4/2018 | Stark | ......................... | B62B 3/02 |
| 10,117,638 B2 * | 11/2018 | Stankard | .................. | H05K 5/00 |
| 10,453,572 B1 * | 10/2019 | Brooks | .................. | G16H 40/40 |
| 11,642,102 B2 * | 5/2023 | Eda | ....................... | A61B 8/4405 |
| | | | | 248/52 |
| 11,678,864 B2 * | 6/2023 | Meurer | .................... | A61B 8/42 |
| | | | | 600/459 |
| 11,751,845 B2 * | 9/2023 | Nally | ................... | A61B 8/4405 |
| | | | | 600/459 |

(Continued)

*Primary Examiner* — Patrick D Hawn
(74) *Attorney, Agent, or Firm* — Boyle Fredrickson S.C.

(57) ABSTRACT

A portable ultrasound imaging assembly includes a cart or support stand on which is mounted a portable ultrasound imaging system and a handle that can be grasped by a user to move the cart and imaging assembly into the desired position. The support stand further includes a storage bin removably mounted in a readily accessible location directly below the handle. The storage bin is formed to hold a number of large containers, such as cylindrical sanitizing wipe canisters, and has a profile similar to that of the handle. The profile of the storage bin includes a rear facing recess within which the support stand is disposed when the storage bin is secured to the support stand in either a forward or rearward facing direction. The attachment structure(s) for the storage bin is located within the recess to minimizing the profile of the storage bin on the support stand.

18 Claims, 9 Drawing Sheets

(56) References Cited

U.S. PATENT DOCUMENTS

| | | | |
|---|---|---|---|
| 2006/0207955 A1* | 9/2006 | Ouyang | A47F 5/0043 |
| | | | 211/192 |
| 2015/0025389 A1* | 1/2015 | Murphy | A61B 8/4455 |
| | | | 600/459 |
| 2018/0201289 A1* | 7/2018 | Sakakibara | B62B 3/005 |
| 2019/0380681 A1 | 12/2019 | Meurer et al. | |
| 2020/0367857 A1* | 11/2020 | Teraishi | A61B 8/4209 |
| 2021/0106309 A1* | 4/2021 | Mesaros | A61B 8/4405 |

\* cited by examiner

REVERSIBLE CART MOUNTED STORAGE BIN

BACKGROUND OF THE INVENTION

Embodiments of the subject matter disclosed herein relate to diagnostic medical imaging, and more particularly, to ultrasound imaging devices and workstations.

An ultrasound imaging system typically includes an ultrasound probe that is applied to a patient's body and a workstation or device that is operably coupled to the probe. The probe may be controlled by an operator of the system and is configured to transmit and receive ultrasound signals that are processed into an ultrasound image by the workstation or device. The workstation or device may show the ultrasound images through a display device. In one example, the display device may be a touch-sensitive display, also referred to as a touchscreen. A user may interact with the touchscreen to analyze the displayed image. For example, a user may use their fingers on the touchscreen to position a region of interest (ROI), place measurement calipers, or the like.

In ultrasound imaging systems that are used as point of care devices, e.g., devices that are mobile and/or that are employed at the patient bedside, or quickly wheeled or carried into tight spaces, in critical and compromising situations, such as emergency rooms or surgical operations, the systems are formed as part of an ultrasound imaging assembly including a support stand or cart that can readily be moved to position the ultrasound imaging system where desired. The ultrasound imaging system can be disposed on the support stand in a manner that enables the ultrasound imaging system to be readily employed to obtain images of the patient at the particular use location. With certain ultrasound imaging systems, components of the imaging system, such as the display device, can be removed from the support stand to further enhance the mobility and utility of the point of care ultrasound imaging system.

In these types of ultrasound imaging assemblies and systems, the support stand or cart must be able to hold a number of items and accessories that are necessary for use with the ultrasound imaging system. These types of items include, but are not limited to, ultrasound gel containers, and sanitizing wipes for cleaning surfaces of the ultrasound system and accessories between procedures, such as the probes and screens of the ultrasound imaging system, among others.

However, the due to the size of the containers or canisters for these types of items, and in particular the sanitizing wipes, the storage locations available on the cart for the portable ultrasound imaging system often do not accommodate the canisters. Therefore, the canisters are often displaced from the cart in inefficient locations, such as in separate locations where the cart must be taken after use to clean and sterilize the ultrasound imaging system between procedures, or must be carried by an individual separately from the cart.

As a result, it is desirable to develop storage devices for a portable ultrasound imaging system and an associated support stand/cart capable of holding items of a larger size in a readily accessible and compact manner to minimize and eliminate these issues with prior art systems.

BRIEF DESCRIPTION OF THE DISCLOSURE

In the present disclosure, a portable ultrasound imaging assembly includes a cart or support stand on which is mounted a portable ultrasound imaging system and a handle that can be grasped by a user to move the cart and imaging assembly into the desired position. The support stand further includes a storage bin removably mounted in a readily accessible location directly below the handle. The storage bin is formed to hold a number of large storage containers, such as cylindrical sanitizing wipe canisters, and has a profile similar to that of the handle. The profile of the storage bin includes a rear facing recess within which the support stand is disposed when the storage bin is secured to the support stand in either a forward or rearward facing direction. The attachment structure(s) for the storage bin is also located within the recess to maximize the storage capacity of the storage bin while minimizing the profile of the storage bin on the support stand.

According to another aspect of the disclosure, A storage bin for a portable ultrasound imaging system includes a bottom wall having a front end and a rear end and a side wall extending upwardly from the bottom wall around the periphery of the bottom wall to define an interior of the storage bin, wherein the bottom wall and the side wall define a recess extending into the interior from the rear end, and wherein at least a portion of the support stand is adapted to be removably positioned within the recess in a forward or rearward mounting direction for the storage bin.

According to another aspect of the disclosure, a support structure for a portable ultrasound imaging system includes a support stand, a number of securing structures disposed on the support stand and a storage bin removably attached to the support stand, the storage bin including a number of attachment structures thereon that are engageable with the number of securing structures to mount the storage bin on the support stand, wherein the storage bin can be mounted to the support stand in either of a pair of oppositely facing mounting directions.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The foregoing summary, as well as the following detailed description of certain embodiments of the present invention, will be better understood when read in conjunction with the appended drawings. As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 1:
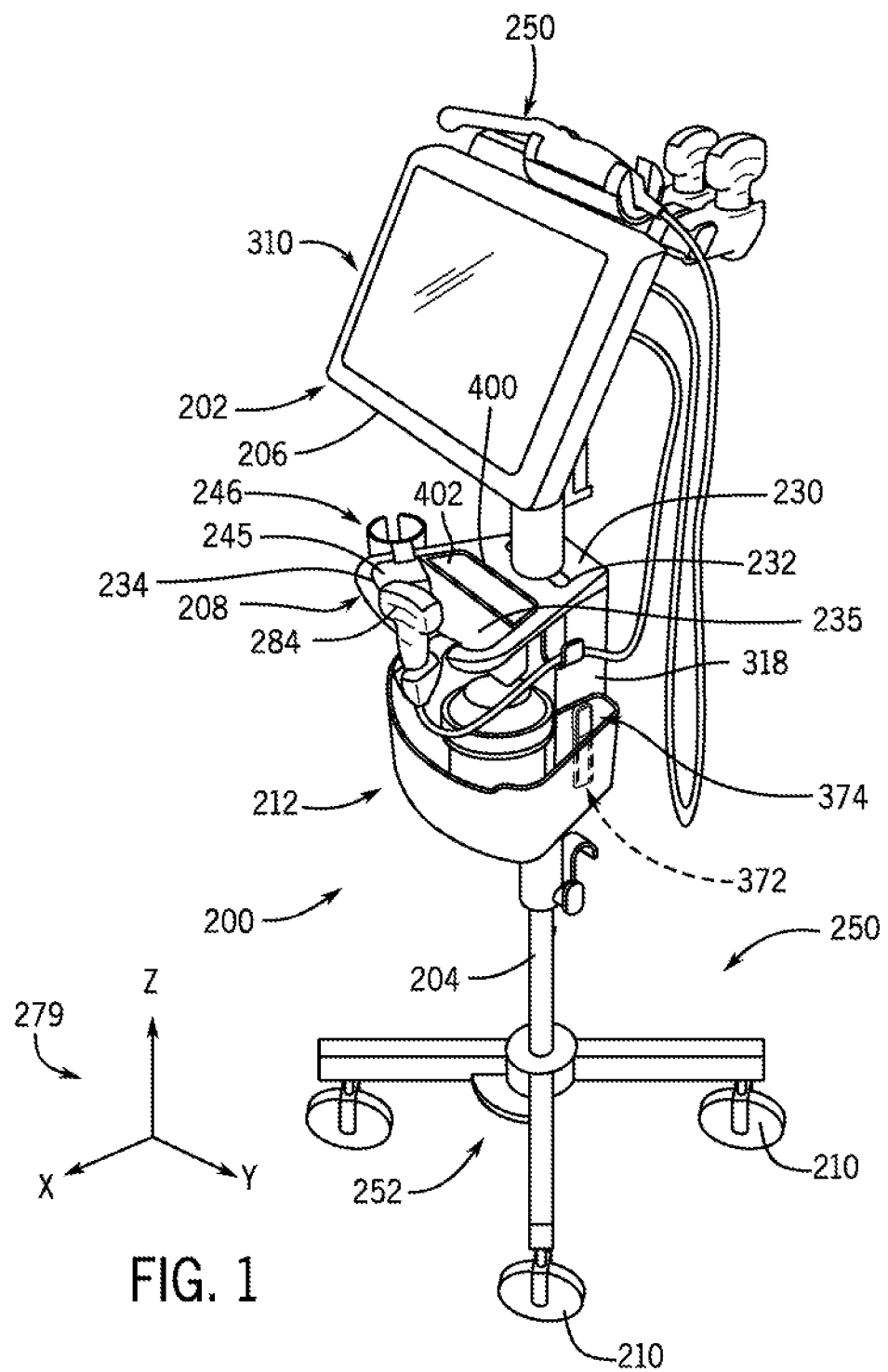
FIG. 1 is an isometric view of a portable ultrasound imaging assembly including a storage bin, according to an embodiment of the invention.
Figure 2:
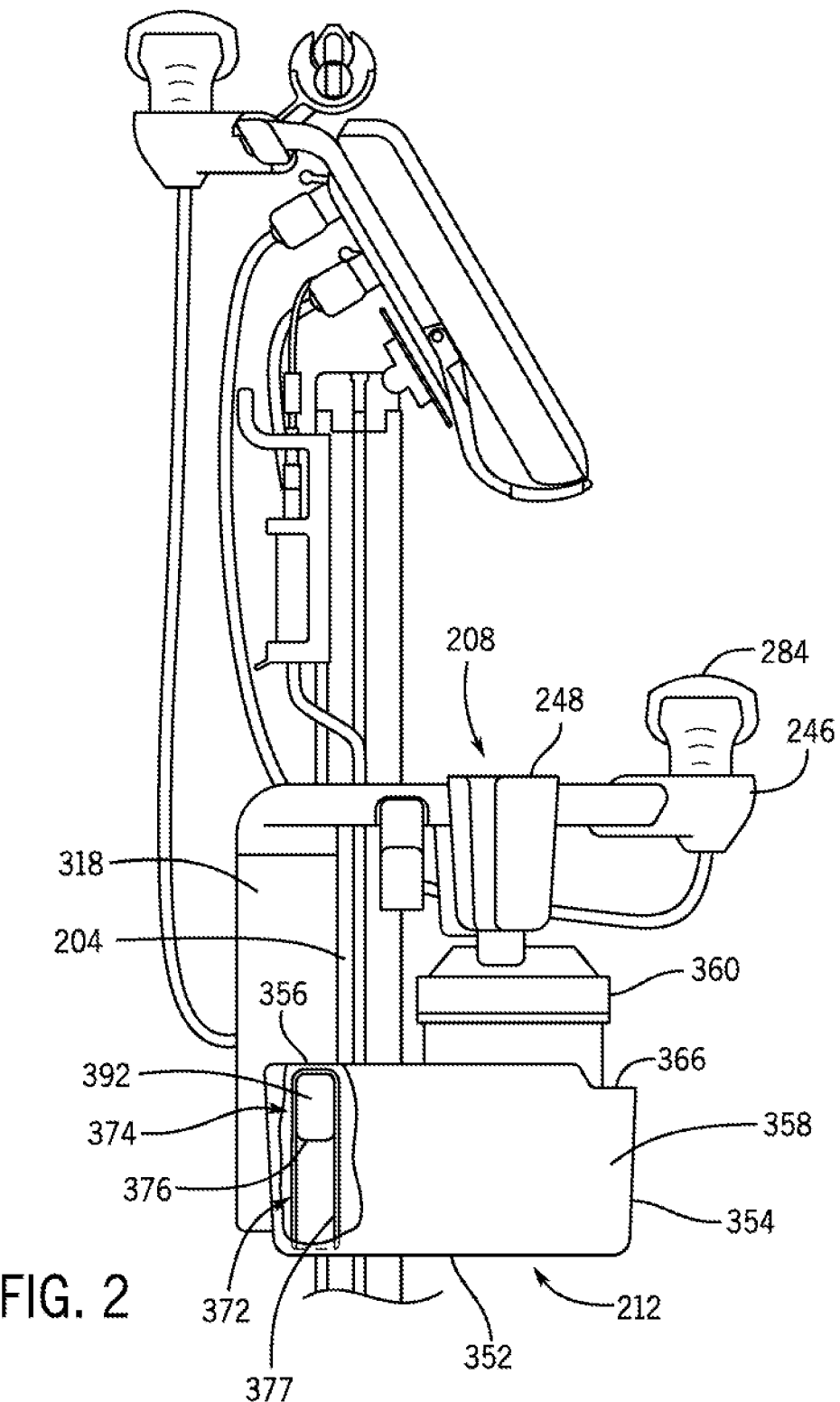
FIG. 2 is a partially broken away, side elevation view of the portable ultrasound imaging assembly and a front-mounted storage bin, in accordance with an embodiment.
Figure 3:
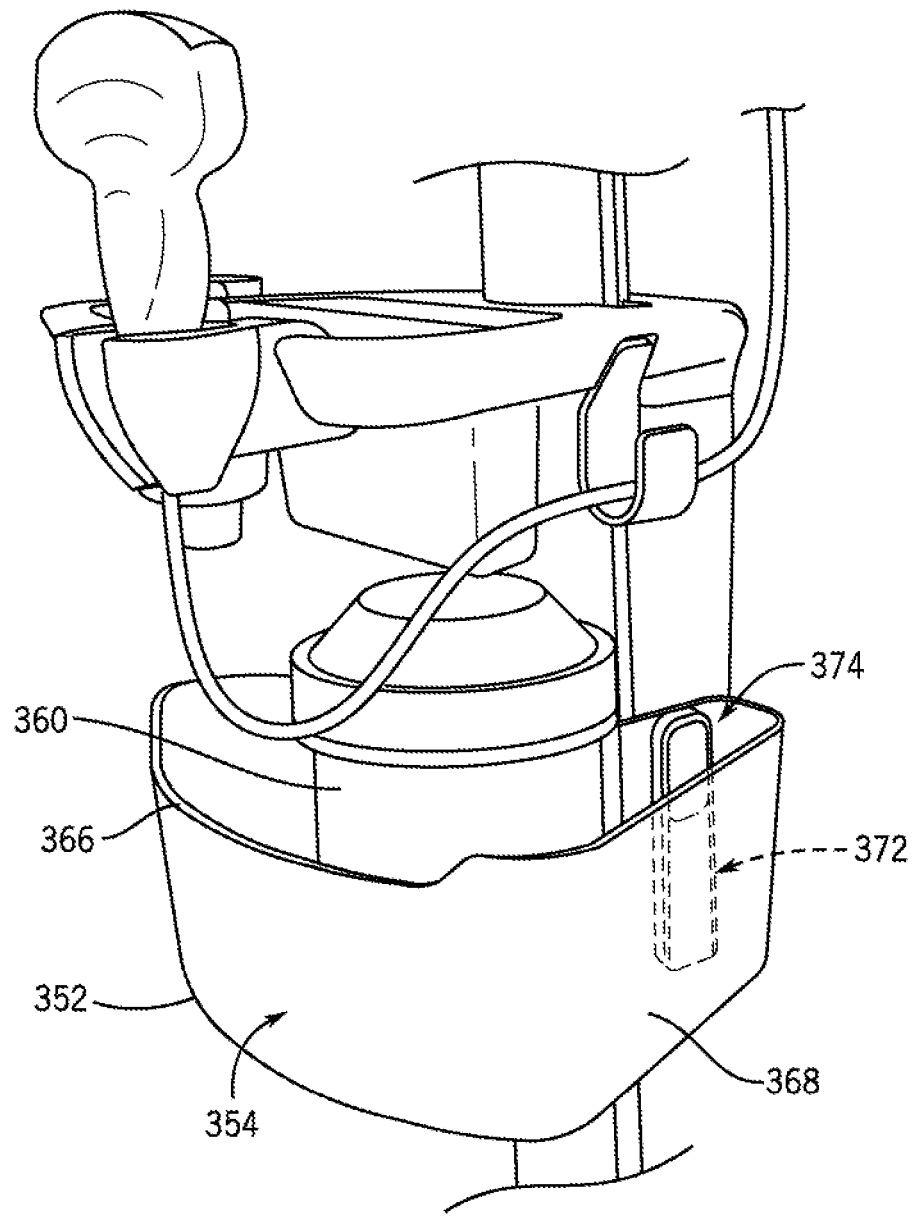
FIG. 3 is a partially broken away, front perspective view of the front-mounted storage bin of FIG. 2 in accordance with an embodiment.
Figure 4:
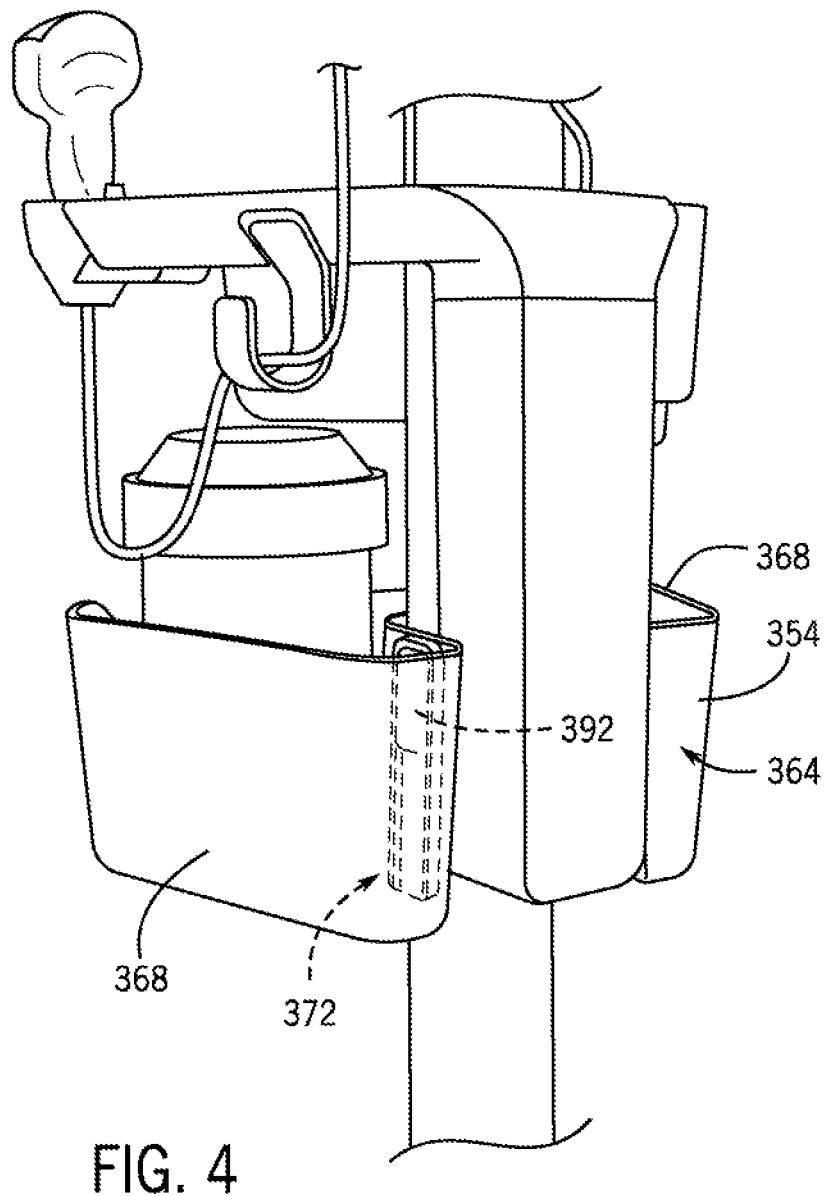
FIG. 4 is a partially broken away, rear perspective view of the front-mounted storage bin of FIG. 2 in accordance with an embodiment.

As shown in FIG. 1, an ultrasound imaging assembly 200 is shown. The ultrasound imaging assembly 200 includes portable ultrasound system 202. In one example, the portable ultrasound system 202 is similar to that disclosed in US Patent Application Publication No. US2019/0380681 entitled Method And Systems For A Portable Ultrasound Imaging System, the entirety of which is expressly incorporated herein by reference for all purposes. The portable ultrasound system 202 is a unitary system that is capable of being separated (e.g., decoupled) from a remainder of the ultrasound imaging assembly 200 and may be moved (e.g., portably) from room to room relative to the remainder of the ultrasound imaging assembly 200 which may stay in place and/or not be moved with the portable ultrasound system 202.

The ultrasound imaging assembly 200 includes support stand 204, and each of a central handle 208, a storage container or bin 212, and cradle 206 coupled to the support stand 204. Specifically, the central handle 208 and the storage bin 212 are shown coupled to the support stand 204 between a first end 250 and a second end 252, with the cradle 206 positioned at the first end 250. The cradle 206 supports a portable ultrasound imaging device 310 including a display and touch screen 312, and a number of imaging probes 284 supported on the device 310 and operably connected to the imaging device 310 by cords 286.

The support stand 204 also includes a plurality of casters 210 positioned at the second end 252. Casters 210 are configured to support the support stand 204 against ground surface 260 and to enable the support stand 204 to more easily move across the ground surface 260 (e.g., roll along the ground surface 260). The z-axis of reference axes 279 is an axis positioned vertical relative to the ground surface 260 (e.g., extending in a vertical, normal direction relative to ground surface 260). In some examples, one or more of the casters 210 may be configured with a locking mechanism (e.g., a brake) configured to selectively lock the casters 210 and maintain a position of the support stand 204 relative to the ground surface 260 (e.g., reduce a likelihood of the casters 210 from rolling or otherwise moving relative to the ground surface 260).

FIG. 1 additionally shows the central handle 208 coupled to the support stand 204 of the ultrasound imaging assembly 200. The handle 208 includes a body 230 that defines an opening 232 shaped complementary to the shape of the support stand 204, such that the stand 204 can extend through and engage body 230 at the opening 232. A steering bar 234 extends outwardly from the body 230 and defines an aperture 235 between the bar 234 and the body 230. The aperture 235 can include a suitable engagement structure, such as an inwardly sloped inner surface 245, that can engage a complementary structure, such as a curved collar 400, of a container 402 positionable within the aperture 235 adjacent the body 230 to provide additional storage locations for the assembly 200, while maintaining the utility of the steering bar 234. The bar 234 also supports a number of accessory holders 246 that are attached to the bar 234 at perches or holder attachment locations 248 to hold additional items, such as ultrasound gel containers (not shown) or imaging probes 284 therein.

Looking now at FIGS. 1-6, the storage bin 212 is includes a body 350 formed of any suitable material, such as a plastic material, but in one exemplary embodiment is formed of a translucent or transparent plastic and/or resin material, in order to minimize the appearance of the bin 212, particularly when empty. The body 350 has a bottom wall 352, a side wall 354 that extends upwardly from the bottom wall 352, and an open top end 356. The side wall 354 extends continuously around the perimeter of the bottom wall 352 to form an interior 358 for the storage container 212 within which a number of canisters 360 can be positioned.

Figure 5:
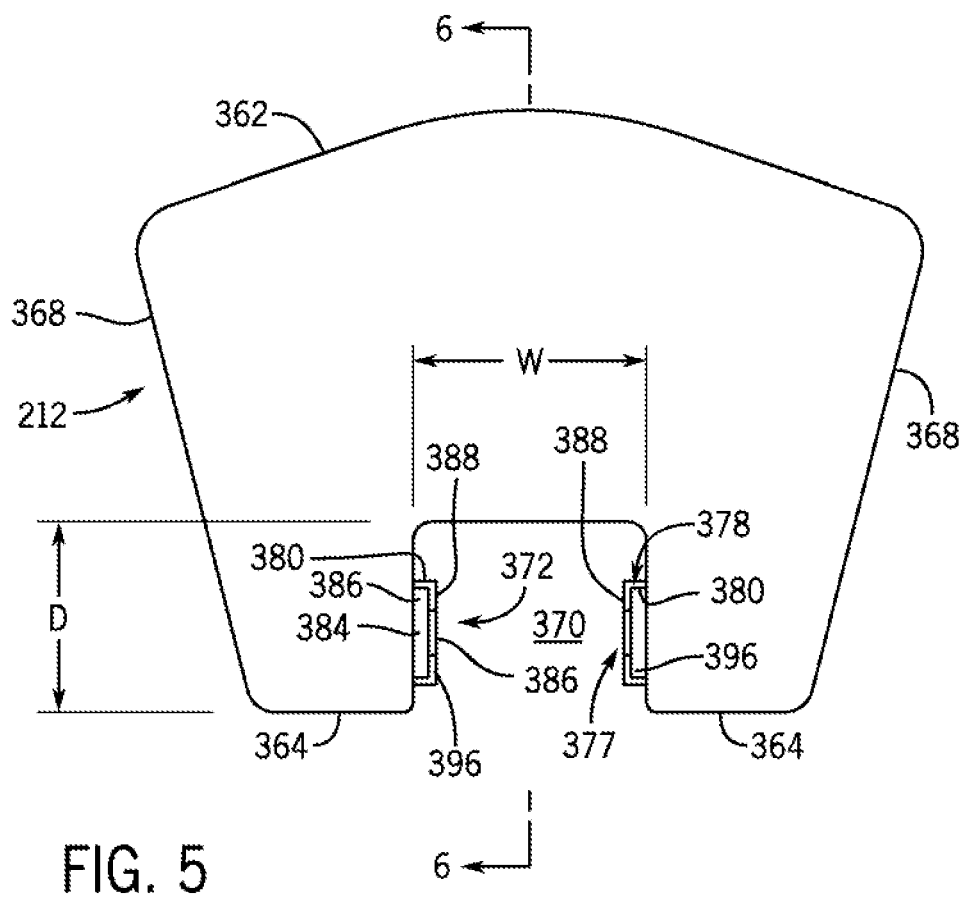
FIG. 5 is an isometric view of the storage bin of FIG. 2.
Figure 6:
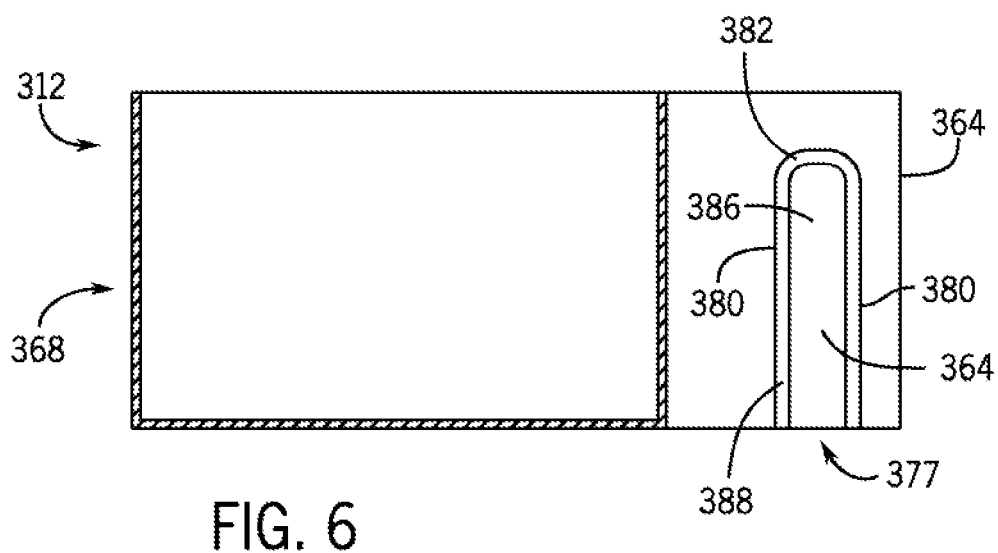
FIG. 6 is a cross-sectional view along line 6-6 of FIG. 5.

As best shown in the exemplary illustrated embodiment of FIGS. 5 and 6, the storage bin 212 includes a wide front end 362 and a narrow rear end 364 joined by planar sides 368 to provide a tapered geometry from the front end 362 to the rear end 364. This tapered geometry for or periphery of the bin 212 conforms to, and optionally mirrors the shape or perimeter of the central handle 208, such that the bin 212 does not increase the profile of the assembly 200 when mounted to the support stand 204 beneath the handle 208. In addition, the tapered geometry provides a friction fit to the canisters 360 disposed within the interior 358 of the bin 212, such that the canisters 360 do not slide or shift within the bin 212 during transport of the assembly 200. For example, in the illustrated exemplary embodiment of FIG. 5, the front end 362 is curved along an arc that is complementary to that of the exterior of the cylindrical canister 360. Thus, the curved front end 362, in conjunction with the sides 368, the recess 370 formed in the rear end 364 and the flat sections of the side wall 354 to each side of the recess 370, operates to frictionally engage multiple exterior surfaces of the cylindrical canisters 360 to prevent the canisters 360 from sliding within the interior 358 of the bin 212 as the cart support stand 204 to which the bin 212 is mounted is moved.

The front end 362 also includes a notch or reduced height section 366 centered on the front end 362. This reduced height section 366 extends along the front end 362 between opposed sides 368 of the bin 212 and provides sufficient clearance between the side wall 354 and the handle 208 to enable the canisters 360 to be easily placed within and/or removed from within the interior 358 of the bin 212, even when the bin 212 is mounted directly below the handle 208.

Opposite the reduced height section 366, the bottom wall 352 and side wall 354 at the rear end 364 define a recess 370 extending into the interior 358 from the rear end 364 towards the front end 362. The recess 370 extends from the bottom wall 352 to the open top end 356 and has a width W, i.e., the distance between the sections of the rear end 264 on opposite sides of the recess 370, that conforms to the width of the support stand 204 or the power supply/power supply carrier 318 mounted to the support stand 204 along the Y axis. As such, the recess 370 can be positioned in close conformance around the support stand 204 and/or power supply 318 when the bin 212 is attached to the support stand 204.

Further, the depth D of the recess 370, or the distance the recess 370 extends towards the front end 362 from the rear end 364, corresponds to the combined thickness along the X axis of the support stand 204 and/or at least a portion a power supply/power supply carrier 318 secured to the support stand 204 at a location below and generally opposite the steering bar 234. As such, the recess 370 encompasses the support stand 204 and/or at least a portion of the power supply 318 when secured to the support stand 204, thereby maximizing the storage area provided by the interior 358 of the bin 212 while not expanding the profile of the bin 212 beyond that of the handle 208.

Looking now at FIGS. 5-7C, to secure the bin 212 to the support stand 204, the recess 370 includes an attachment structure 372 located within the recess 370 that is mateable with a securing structure 374 disposed on the support stand 204 and/or the power supply 318. The securing structure 374 includes a pair of securing members 376 disposed on opposite sides of the support stand 204 and/or power supply 318 that can engage and hold the attachment structures 372 on the bin 212. The location of the securing structures 374 on the support stand 204/power supply 318, in conjunction with the dimensions of the recess 370 described previously, enable the bin 212 to be mounted using the attachment structures 372 in a front-mounted position directly beneath the handle 208 (FIGS. 1-4) or in a rear-mounted position, (FIGS. 7A-10) where the bin 212 is disposed opposite the handle 208.

Figure 7A:
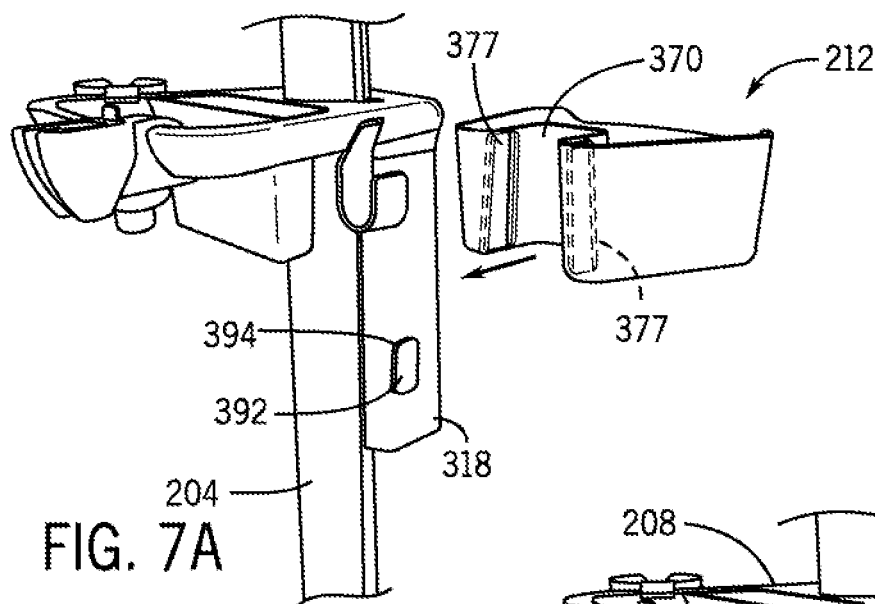
FIGS. 7A-7C are isometric views of the attachment of the storage bin of FIG. 1 to the support stand of the portable ultrasound imaging assembly, in accordance with an embodiment.
Figure 7B:
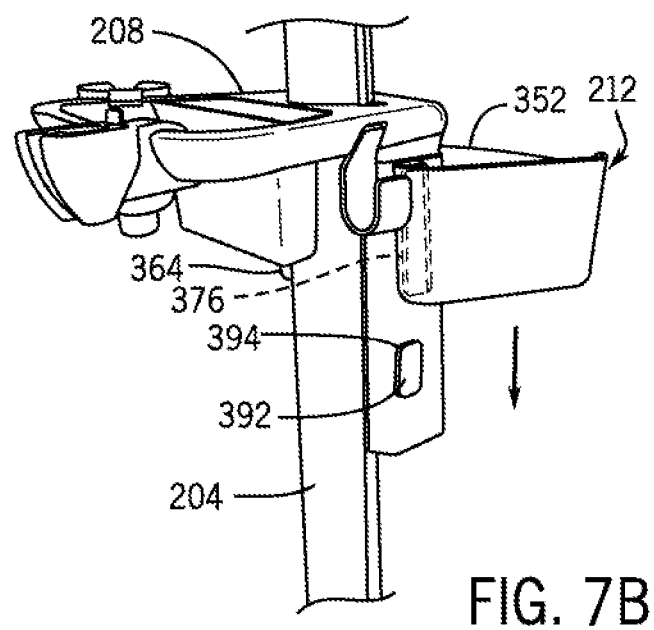
Figure 7C:
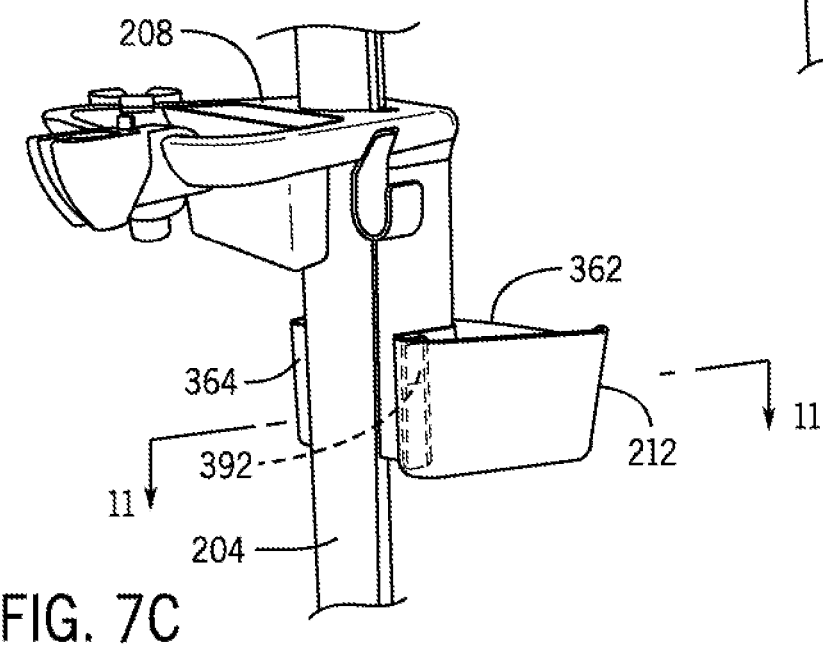
Figure 8:
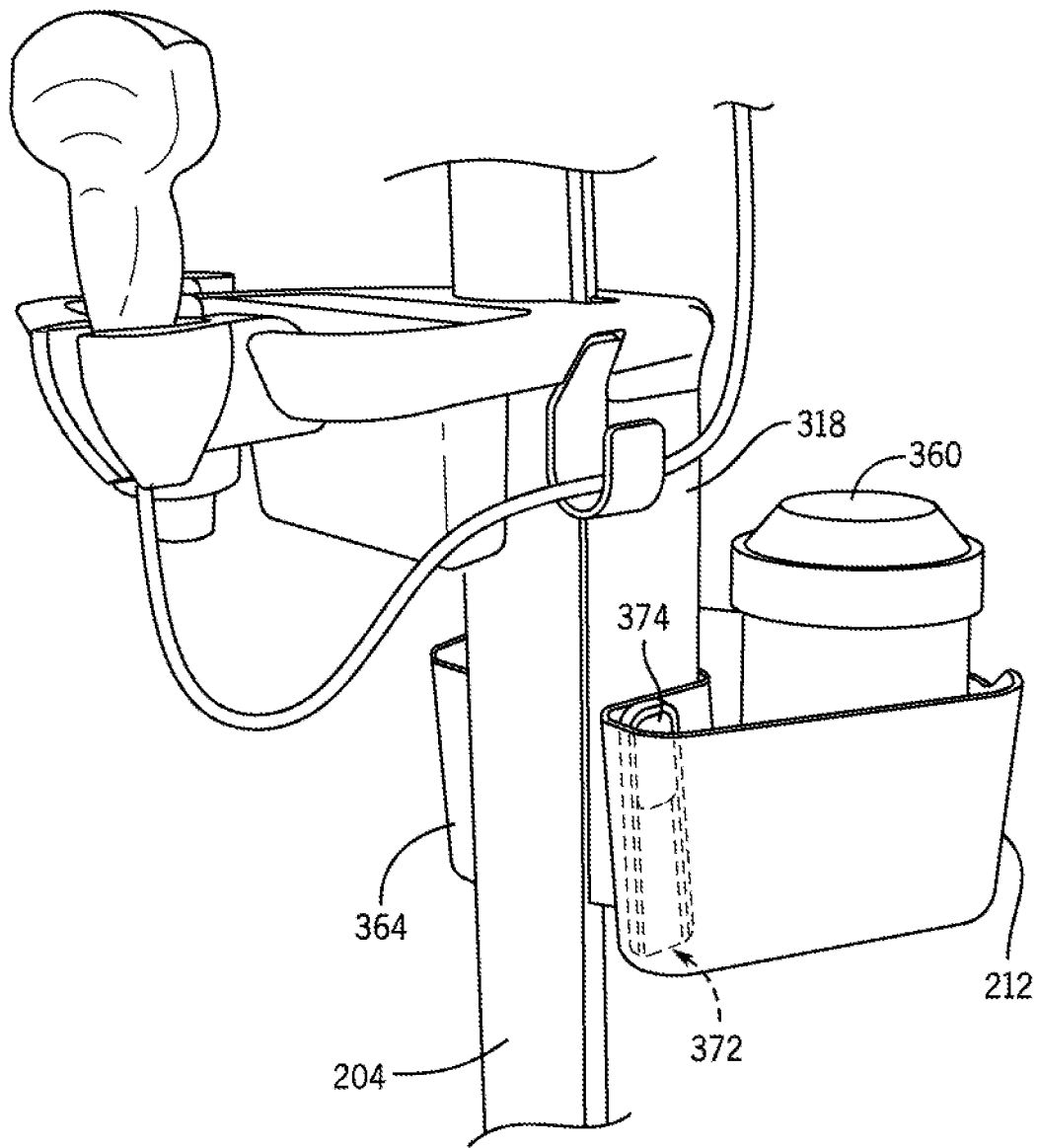
FIG. 8 is a partially broken away, front perspective view of a rear-mounted storage bin of FIG. 2 in accordance with an embodiment.
Figure 9:
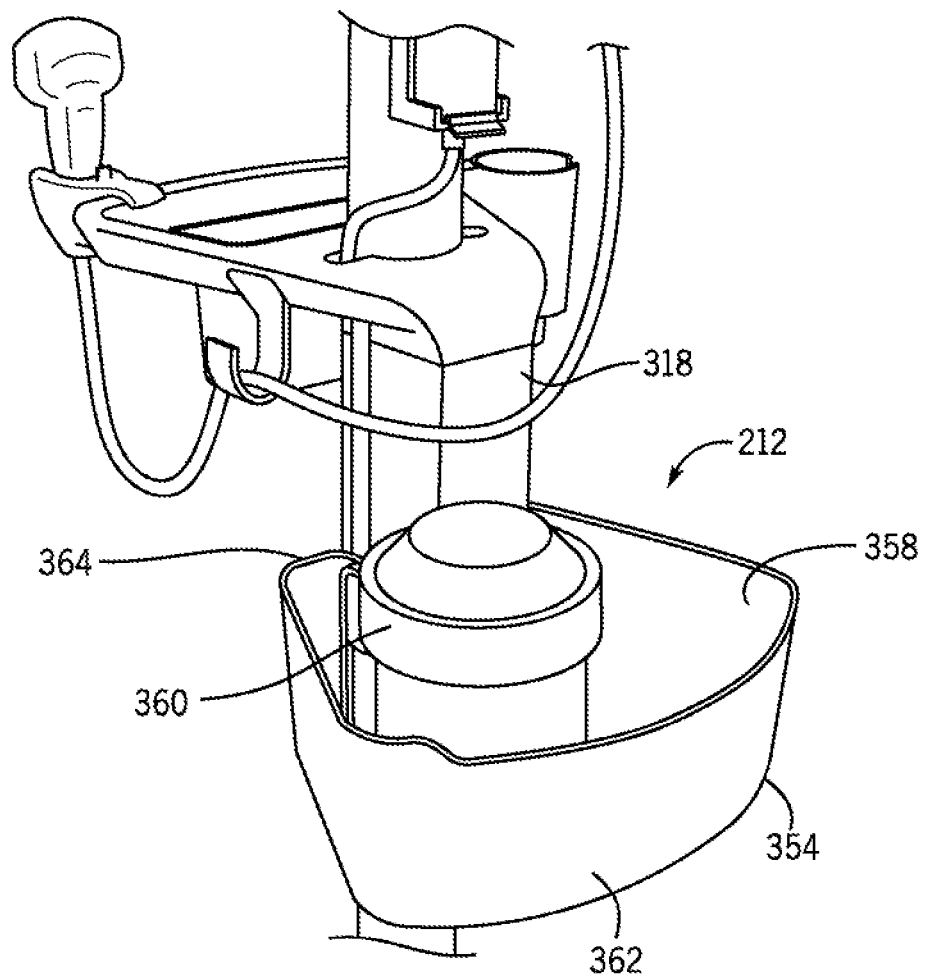
FIG. 9 is a partially broken away, rear perspective view of the storage bin of FIG. 8 in accordance with an embodiment.
Figure 10:
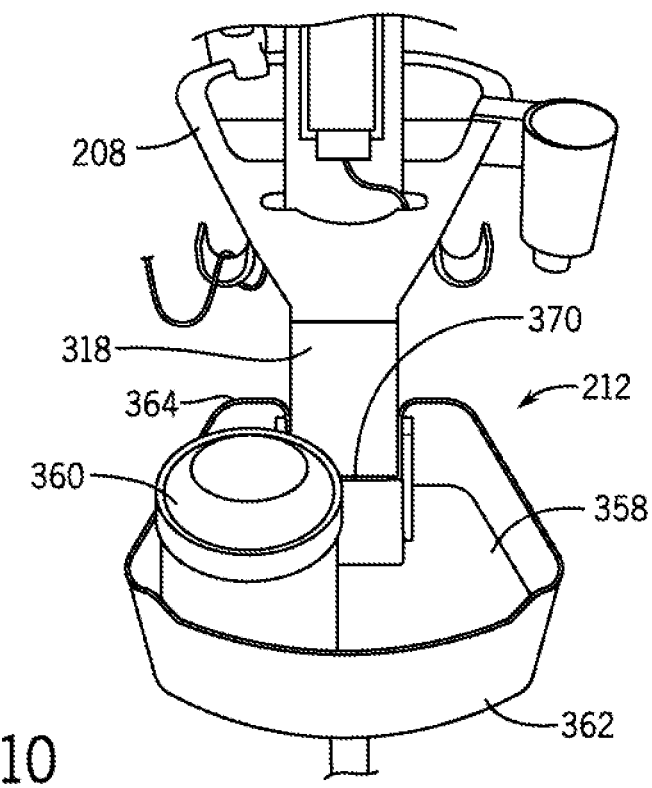
FIG. 10 is a partially broken away, top plan view of the storage bin of FIG. 8 in accordance with an embodiment.

For either mounting position, as best shown in FIGS. 7A-7C, to attach mount the bin 212 to the support stand 204, initially the recess 370 is positioned at least partially around one of the support stand 204 and/or the power supply 318 to align the attachment structures 372 on opposite sides of the recess 370 with the securing structures 374 located on opposite sides of the support stand 204 or power supply 318 (FIG. 7A). The bin 212 is then lowered to engage the attachment structures 372 with the securing structures 374 and hold the bin 212 on the support stand 204 in the selected front mounted or rear mounted configuration (FIG. 7B). The bin 212 can additionally be removed from the support stand 204 by lifting the bin 212 relative to the support stand 204 to disengage the attachment structures 372 from the securing structures 374 in an opposed manner (FIG. 7C).

In the exemplary illustrated embodiment of FIGS. 5-7C, the attachment structures 372 are shown as being formed of a pair of attachment channels 377 disposed on opposite sides of the recess 370. Each channel 377 is formed of a ridge 378, e.g., a U-shaped ridge 378 with a pair of opposed sides 380 and a curved top portion 382 joining the sides 380, that extends into the recess 370 from each portion of the side wall 354 on opposite sides of the recess 370 to define an interior 384 and an open end 386 adjacent the bottom wall 352 of the bin 212. A lip 388 extends inwardly from the ridge 378 to cover a portion of the interior 384 along the periphery of the ridge 378, while leaving a central portion 390 of the interior 384 exposed.

The corresponding securing structures 374 are formed as tabs 392 spaced from and secured to opposed sides of the support stand 204/power supply 318 by stems 394 extending between the support stand 204/power supply 318 and the tabs 392. The tabs 392 each have a width slightly less than the distance between the opposed straight sides 380 of the ridge 378, and a thickness slightly less than the distance of the interior 384 between the side wall 354 and the lip 388. The length of the tabs 392 can be selected as desired, but need only be large enough to enable the tabs 392 to engage a sufficient length of the lip 388 to securely hold the attachment structure 372 on the securing structure 374.

Figure 11:
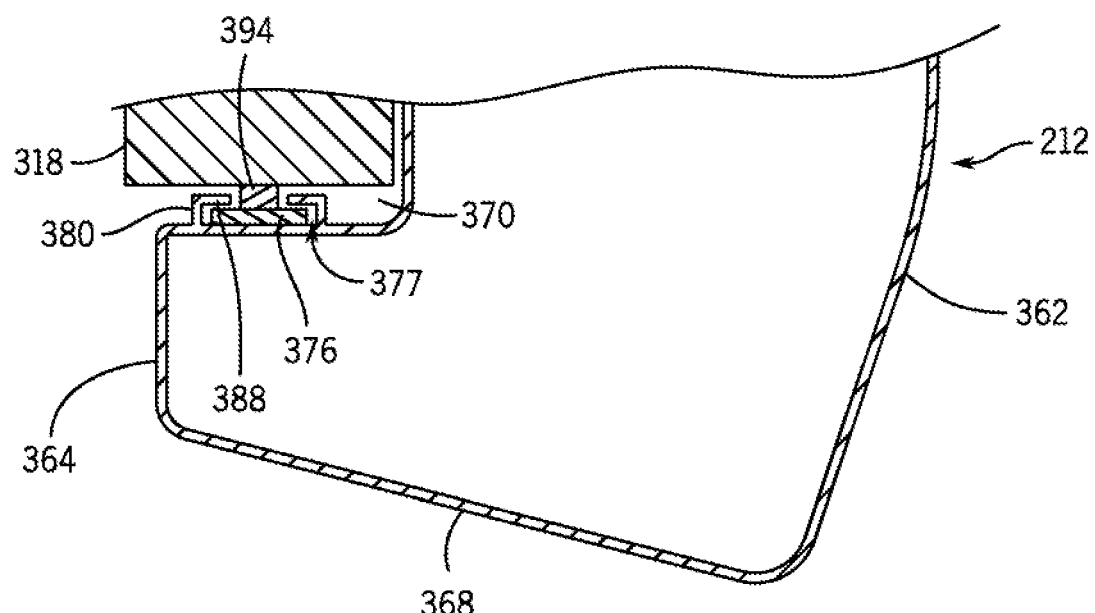
FIG. 11 is a cross-sectional view along line 11-11 of FIG. 7C.

With this construction, to mount the bin 212 the channels 377 are positioned over the tabs 392. The bin 212 can then be lowered to position the sides of the tabs 392 within the spaces 396 defined between the lip 388 and the side wall 354 of each channel 377. The bin 212 is continued to be lowered until the upper end 398 of the tab 392, which in the exemplary illustrated embodiment is shaped to conform to the shape of the curved top portion 382 of the channel 377, which functions as a stop for the insertion of the tab 392 into the channel 377, as shown in FIG. 11. In this position numerous items, including canisters 360 can be placed in the bins 212, with the weight of the canisters 360 enhancing the engagement of the bin 212 with the tabs 32.

In addition, in an alternative embodiment, the position of the securing structures 374/tabs 392 on the support stand 204/power supply 318 is on a portion of the support stand 204 that can be raised and lowered using a suitable mechanism on the support stand 204, such that the mounting position of the bin 212 moves along with the handle 208 on the support stand 204, whether in a front mount or rear mount position on the support stand 204/power supply 318.

In an additional exemplary embodiment, as a result of the readily switchable and replaceable nature of the mounting structure for the storage bin 212, in certain embodiment multiple bins 212 can be preloaded with required supplies for different procedures to be performed using the portable ultrasound imaging assembly 200. The bins 212 can be reversed on the support stand 204 and/or removed and replaced with additional preloaded bins 212 in order to streamline the performance of the different procedures using the assembly 200.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A support structure for a portable ultrasound imaging system, comprising:
   a support stand to which is mounted a portable ultrasound imaging system;
   a number of securing structures disposed on the support stand; and
   a storage bin removably attached to the support stand, the storage bin including a number of attachment structures thereon that are engageable with the number of securing structures to mount the storage bin on the support stand,
wherein the storage bin can be mounted to the support stand in either of a pair of oppositely facing mounting directions, wherein the storage bin comprises:
   a bottom wall having a front end and a rear end; and
   a side wall extending upwardly from the bottom wall around the periphery of the bottom wall to define an interior of the storage bin,
   wherein the bottom wall and the side wall define a recess extending into the interior from the rear end, wherein portions of the interior of the storage bin are disposed on opposed sides of the recess, and wherein at least a portion of the support stand is removably disposed within the recess in either mounting direction.

2. The support structure of claim 1, wherein the number of attachment structures are disposed within the recess.

3. The support structure of claim 2, wherein the number of attachment structures are disposed on facing surfaces of the recess.

4. The support structure of claim 3, wherein the number of attachment structures comprise a pair of channels disposed on facing surfaces of the recess.

5. The support structure of claim 4, wherein the channels comprise:
   a ridge disposed on and extending outwardly from the side wall; and
   a lip disposed on the ridge opposite the side wall and extending perpendicularly to the ridge to define a space between the lip and the side wall.

6. The support structure of claim 5, wherein the ridge comprises:
   a pair of straight sides defining an open end adjacent the bottom wall; and
   a curved end joining the sides opposite the open end.

7. The support structure of claim 4, wherein the number of securing structures comprise:
   a stem connected to and extending outwardly from the support stand; and
   a tab disposed on the stem opposite the support stand.

8. The support structure of claim 7, wherein the tab is disposed perpendicularly to the stem.

9. The support structure of claim 8, wherein the tab has a profile complementary to an interior profile of the channel.

10. The support structure of claim 7, wherein the number of securing structures are disposed on oppositely facing surfaces of the support stand.

11. The support structure of claim 1, wherein the side wall forming the front end is curved.

12. The support structure of claim 1, wherein the side wall forming the front end includes a reduced height section therein.

13. The support structure of claim 1, comprising:
   a central handle secured to the support stand above the storage bin,
   wherein the periphery of the storage bin mirrors the perimeter of the central handle.

14. The support structure of claim 1, wherein the number of securing structures are disposed on a vertically adjustable portion of the support stand.

15. A storage bin for a portable ultrasound imaging system, comprising:
   a bottom wall having a front end and a rear end; and
   a side wall extending upwardly from the bottom wall around the periphery of the bottom wall to define an interior of the storage bin,
wherein the bottom wall and the side wall define a recess extending into the interior from the rear end, the recess including a number of attachment structures thereon adapted to be removably engaged with at least a portion of a support stand positioned within the recess in a forward or rearward mounting direction for the storage bin,
wherein the number of attachment structures comprise a pair of channels disposed on facing surfaces of the recess,
wherein the pair of channels comprise:
   a ridge disposed on and extending outwardly from the side wall; and
   a lip disposed on the ridge opposite the side wall and extending perpendicularly to the ridge to define a space between the lip and the side wall, and
wherein the ridge comprises:
   a pair of straight sides defining an open end adjacent the bottom wall; and
   a curved end joining the sides opposite the open end.

16. The storage bin of claim 15, wherein the interior of the storage bin is configured to secure a canister disposed within the interior.

17. The storage bin of claim 16, wherein the side wall forming the front end is curved.

18. The storage bin of claim 17, wherein the side wall forming the rear end to each side of the recess is flat.

* * * * *